United States Patent
Chen et al.

(10) Patent No.: US 10,082,565 B2
(45) Date of Patent: Sep. 25, 2018

(54) MULTILEVEL BIPOLAR PULSER

(71) Applicant: Butterfly Network, Inc., Guilford, CT (US)

(72) Inventors: Kailiang Chen, Guilford, CT (US); Tyler S. Ralston, Clinton, CT (US); Keith G. Fife, Palo Alto, CA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 15/087,914

(22) Filed: Mar. 31, 2016

(65) Prior Publication Data
US 2017/0285155 A1    Oct. 5, 2017

(51) Int. Cl.
| | |
|---|---|
| *G01S 7/52* | (2006.01) |
| *G01S 7/521* | (2006.01) |
| *G01S 15/89* | (2006.01) |
| *A61B 7/04* | (2006.01) |

(52) U.S. Cl.
CPC .......... *G01S 7/52022* (2013.01); *G01S 7/521* (2013.01); *G01S 7/5202* (2013.01); *G01S 7/5208* (2013.01); *G01S 7/52017* (2013.01); *G01S 7/52047* (2013.01); *G01S 15/8915* (2013.01); *G01S 15/8977* (2013.01); *A61B 7/04* (2013.01)

(58) Field of Classification Search
CPC .. G01S 7/52022; G01S 7/52047; G01S 7/521; G01S 15/8977; A61B 7/04
USPC ....................................................... 367/135
See application file for complete search history.

(56) References Cited

U.S. PATENT DOCUMENTS

| | | | | |
|---|---|---|---|---|
| 4,357,690 A | * | 11/1982 | Kuroda | ................... A61B 10/00 310/317 |
| 4,447,783 A | * | 5/1984 | Quick | ....................... H03L 5/02 323/275 |
| 4,864,547 A | | 9/1989 | Krsna | |
| 5,406,503 A | * | 4/1995 | Williams, Jr. | ...... A61F 9/00745 604/22 |
| 5,892,315 A | * | 4/1999 | Gipson | .................. B06B 1/0246 310/317 |
| 6,241,676 B1 | * | 6/2001 | Savord | ................... B06B 1/0238 600/447 |
| 7,313,053 B2 | | 12/2007 | Wodnicki | |

(Continued)

FOREIGN PATENT DOCUMENTS

| | | |
|---|---|---|
| WO | WO 2009/135255 A1 | 11/2009 |
| WO | WO 2016/057622 A1 | 4/2016 |
| WO | WO 2016/057631 A1 | 4/2016 |

OTHER PUBLICATIONS

Agarwal et al., Single-Chip Solution for Ultrasound Imaging Systems: Initial Results. 2007 IEEE Ultrasonics Symposium. Oct. 1, 2007;1563-6.

(Continued)

*Primary Examiner* — Isam A Alsomiri
*Assistant Examiner* — Amie M Ndure
(74) *Attorney, Agent, or Firm* — Wolf, Greenfield & Sacks, P.C.

(57) ABSTRACT

Circuitry for ultrasound devices is described. A multilevel pulser is described, which can provide bipolar pulses of multiple levels. The multilevel pulser includes a pulsing circuit and pulser and feedback circuit. Symmetric switches are also described. The symmetric switches can be positioned as inputs to ultrasound receiving circuitry to block signals from the receiving circuitry.

18 Claims, 11 Drawing Sheets

(56) References Cited

U.S. PATENT DOCUMENTS

| | | | |
|---|---|---|---|
| 7,549,961 B1 | 6/2009 | Hwang | |
| 7,775,979 B2* | 8/2010 | Thomenius | G01S 7/5208 600/437 |
| 7,859,941 B2* | 12/2010 | Freeman | G01S 7/52025 367/11 |
| 7,883,466 B2* | 2/2011 | Adachi | A61B 8/12 600/407 |
| 8,171,333 B2* | 5/2012 | Ma | G01S 7/5202 367/137 |
| 8,298,144 B2* | 10/2012 | Burcher | A61B 5/0059 600/407 |
| 8,327,521 B2* | 12/2012 | Dirksen | A61B 8/00 257/704 |
| 8,852,103 B2 | 10/2014 | Rothberg et al. | |
| 9,229,097 B2 | 1/2016 | Rothberg et al. | |
| 9,327,142 B2 | 5/2016 | Rothberg et al. | |
| 9,351,706 B2 | 5/2016 | Rothberg et al. | |
| 9,778,348 B1* | 10/2017 | Chen | G01S 7/521 |
| 2003/0097071 A1 | 5/2003 | Halmann et al. | |
| 2005/0007879 A1 | 1/2005 | Nishida | |
| 2005/0131297 A1 | 6/2005 | Nishigaki et al. | |
| 2005/0154300 A1 | 7/2005 | Wodnicki et al. | |
| 2005/0171431 A1* | 8/2005 | Petersen | B06B 1/0223 600/437 |
| 2006/0058588 A1 | 3/2006 | Zdeblick | |
| 2007/0016026 A1* | 1/2007 | Thomenius | G01S 7/5208 600/437 |
| 2007/0083119 A1* | 4/2007 | Adachi | A61B 8/12 600/437 |
| 2007/0242567 A1 | 10/2007 | Daft et al. | |
| 2008/0021327 A1 | 1/2008 | El-Bialy et al. | |
| 2008/0225639 A1* | 9/2008 | Hongou | A61B 8/58 367/13 |
| 2008/0238532 A1 | 10/2008 | Hanazawa et al. | |
| 2009/0096489 A1 | 4/2009 | Ying et al. | |
| 2009/0182233 A1 | 7/2009 | Wodnicki | |
| 2009/0250729 A1 | 10/2009 | Lemmerhirt et al. | |
| 2010/0063399 A1 | 3/2010 | Walker et al. | |
| 2010/0152587 A1 | 6/2010 | Haider et al. | |
| 2010/0228130 A1 | 9/2010 | Chiang et al. | |
| 2010/0317972 A1 | 12/2010 | Baumgartner et al. | |
| 2011/0060225 A1 | 3/2011 | Cogan | |
| 2012/0108963 A1 | 5/2012 | Hara et al. | |
| 2013/0047695 A1 | 2/2013 | Drachmann | |
| 2013/0188457 A1* | 7/2013 | Nielsen | H01L 27/0635 367/135 |
| 2014/0236533 A1 | 8/2014 | Drachmann | |
| 2014/0243614 A1 | 8/2014 | Rothberg et al. | |
| 2014/0288428 A1* | 9/2014 | Rothberg | A61B 8/145 600/447 |
| 2015/0032002 A1 | 1/2015 | Rothberg et al. | |
| 2015/0087977 A1 | 3/2015 | Rothberg et al. | |
| 2015/0297193 A1 | 10/2015 | Rothberg et al. | |
| 2016/0076933 A1 | 3/2016 | Leone et al. | |
| 2016/0331353 A1 | 11/2016 | Ralston et al. | |

OTHER PUBLICATIONS

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

International Search Report and Written Opinion dated Nov. 13, 2014 for Application No. PCT/US2014/032803.

International Search Report and Written Opinion dated Jun. 8, 2017 for Application No. PCT/US2017/025249.

International Search Report and Written Opinion dated Jun. 16, 2017 for Application No. PCT/US2017/025269.

\* cited by examiner

MULTILEVEL BIPOLAR PULSER

BACKGROUND

Field

The present application relates to ultrasound devices for ultrasound imaging and high intensity focused ultrasound (HIFU).

Related Art

Some conventional ultrasound devices include pulsing circuits configured to provide pulses to an ultrasonic transducer. Often the ultrasonic transducer operates in transmission and reception.

BRIEF SUMMARY

Aspects of the present application provide an ultrasound-on-a-chip device including integrated circuitry having a pulser with feedback. Symmetric receive switches are also provided in the ultrasound-on-a-chip device and coupled to an output of the ultrasonic transducers to facilitate the use of multi-level pulsers to drive the ultrasonic transducers.

Aspects of the present application relate to an ultrasound device comprising a capacitive ultrasonic transducer, a pulser having an input terminal and an output terminal, the pulser coupled, at the output terminal, to the capacitive ultrasonic transducer and configured to provide an input signal to the capacitive ultrasonic transducer, and a feedback circuit coupled to the output terminal and the input terminal of the pulser and configured to provide a control signal to the input terminal of the pulser based on a comparison of a detection signal, representing or derived from the input signal, to a threshold voltage.

Aspects of the present application relate to a method of operating an ultrasound device having a capacitive ultrasonic transducer, a pulser coupled to the capacitive ultrasonic transducer and a feedback circuit, the method comprising providing an input signal to the capacitive ultrasonic transducer with the pulser, deriving a detection signal from the input signal, the detection signal representing the input signal, providing a control signal, with the feedback circuit, to the pulser to control the providing of the input signal based on a result obtained by comparing the detection signal to a threshold voltage.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
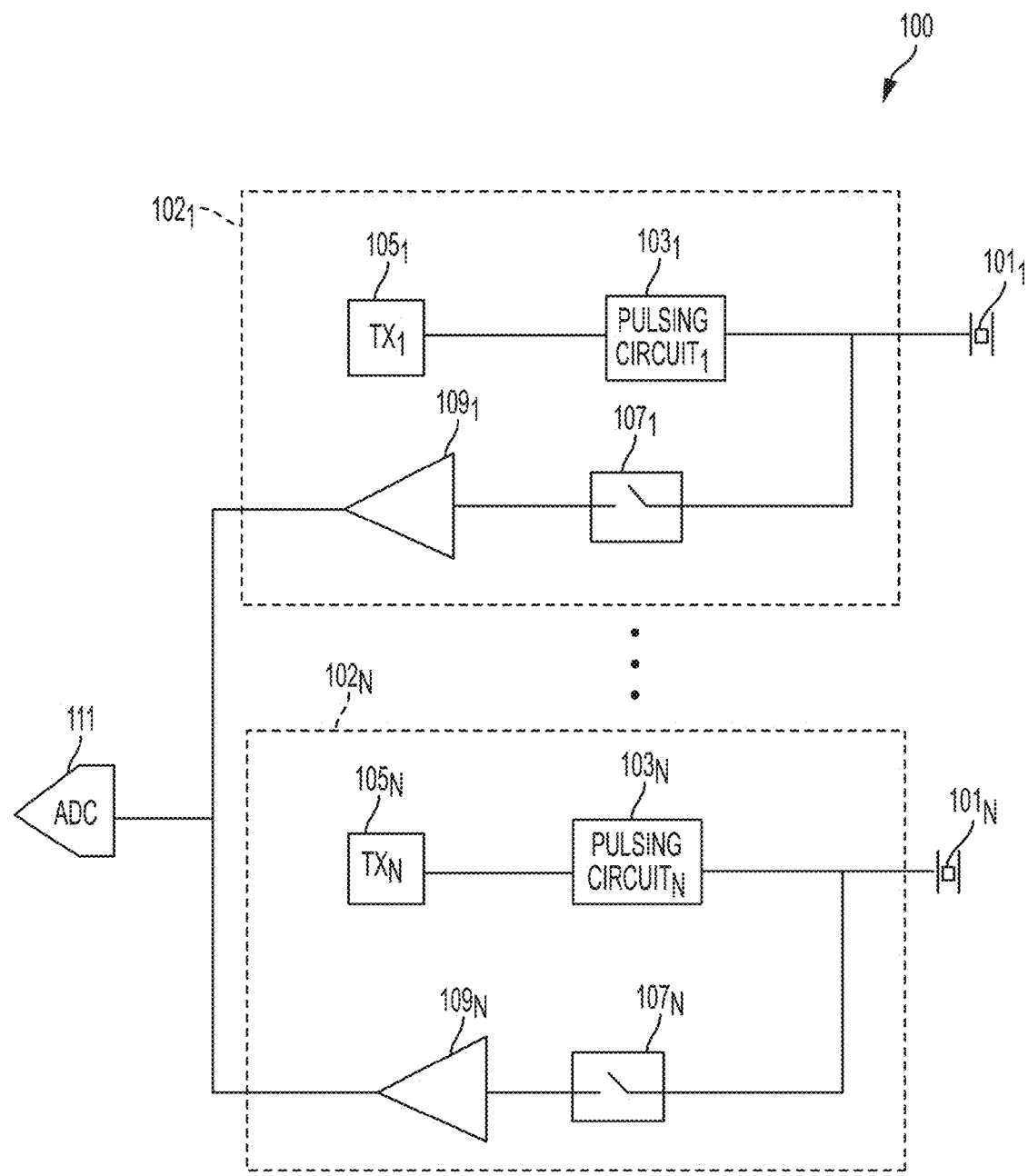
FIG. 1 is a block diagram illustrating an ultrasound device including a plurality of pulsing circuits and a plurality of receiver switches, according to a non-limiting embodiment of the present application.

An ultrasound-on-a-chip device may include ultrasonic transducers integrated with circuitry on a semiconductor die, also referred to herein as a "chip," The ultrasound-on-a-chip device may be employed within an ultrasound probe to perform ultrasound imaging, therapy (e.g., high intensity focused ultrasound (HIFU)), or both. Thus, the circuitry integrated with the ultrasound transducers may support such functions and assume a form appropriate for being employed in a probe or other form factor, such as a stethoscope. The circuitry may include pulsing circuits which generate electrical pulses used to drive the ultrasonic transducers of the ultrasound-on-a-chip device to generate ultrasound signals appropriate for imaging and/or HIFU. The pulsing circuits may be digital, analog, or mixed analog-digital.

Aspects of the present application provide bipolar, multi-level pulsing circuits with feedback. Applicant has appreciated that ultrasound devices configured to transmit unipolar pulses exhibit limited dynamic range because the direct current (DC) component associated with the unipolar pulse may saturate the receiving circuit, thus deteriorating the contrast of the image produced. Unipolar pulses are those which only assume voltages greater than or equal to zero (0), or alternatively, voltages less than or equal to zero (0). Applicant has appreciated that, by contrast, the use of bipolar pulses limits the impact of the DC component and thus provides significantly increased dynamic range and image contrast compared to ultrasound devices utilising unipolar pulses. Thus, aspects of the present application provide ultrasound complementary metal oxide semiconductor (CMOS) chips having circuitry configured to transmit bipolar pulses. Bipolar pulses can assume voltages that are greater than, less than, or equal to zero (0).

The use of multi-level pulsing circuits with feedback arises from Applicant's appreciation that the contrast of ultrasound images may be significantly enhanced by performing time-domain and space-domain apodization of the pulses transmitted to the target being imaged. Apodization may reduce the extent of the side-lobes associated with transmitted pulses, thus increasing the resolution of the image produced. The generation of temporally and spatially apodized pulses may be facilitated by the ability to control signals that can assume multiple values. Multi-level pulses of the type described herein can assume any value selected from among a set of selectable values, where the set may comprise at least three values. The generation of such multi-level pulses may require complicated puller designs where multiple supply voltages are provided. Providing multiple supply voltages may be impractical. This may be especially true when the ultrasound device is to be disposed in a handheld ultrasound probe or other compact form, as additional off-chip supply circuits may be required. Applicant has appreciated that the use of feedback circuits may facilitate the generation of multi-level pulses, and the generation of apodized pulses, without resorting to multiple supply voltages, thus simplifying the design of the ultrasound device.

Aspects of the present application provide ultrasound devices including a symmetric switch coupling an ultrasonic transducer to receiving circuitry. While the use of bipolar pulsing circuits may be beneficial for at least the reasons described above, they can also be detrimental to the ultrasound device's receiving circuitry. The pulses generated by the transmitting circuit may inadvertently electrically couple directly to the receiving circuit, which may not be designed to withstand large positive and negative voltage spikes. As a consequence, the ultrasound device may be damaged if proper protection is not provided. Applicant has appreciated that a suitably positioned symmetric switch designed to block positive and negative voltage spikes associated with bipolar pulses may prevent further damage to receiving circuitry, thus protecting the ultrasound device and facilitating use of bipolar pulsing circuits.

The CMOS circuitry features described above may facilitate creation of an ultrasound-on-a-chip device suitable for performing ultrasound imaging and/or HIFU in a commercially valuable form factor.

The aspects and embodiments described above, as well as additional aspects and embodiments, are described farther below. These aspects and/or embodiments may be used individually, all together, or in any combination of two or more, as the application is not limited in this respect.

As described above, aspects of the present application provide an ultrasound device having a bipolar, multi-level pulsing circuit and a symmetric switch coupling the hi-polar, multi-level pulsing circuit to receive circuitry. FIG. 1 illustrates the general architecture of an ultrasound device which may include such features in accordance with aspects of the present application. The ultrasound device 100 has a plurality of capacitive ultrasonic transducers $101_1 \ldots 101_N$, where N is an integer. Ultrasound device 100 may comprise a plurality of circuitry channels $102_1 \ldots 102_N$. Circuitry channels $102_1 \ldots 102_N$ may be electrically connected to a respective capacitive ultrasonic transducer $101_1 \ldots 101_N$. Ultrasound device 100 may further comprise analog-to-digital converter (ADC) 111.

The capacitive ultrasonic transducers are sensors in some embodiments, producing electrical signals representing received ultrasound signals. The capacitive ultrasonic transducers may also transmit ultrasound signals in some embodiments. The capacitive ultrasonic transducers may be capacitive micromachined ultrasonic transducers (CMUTs) in some embodiments. However, other types of capacitive ultrasonic transducers may be used in other embodiments.

The circuitry channels $102_1 \ldots 102_N$ may include transmit circuitry, receive circuitry, or both. The transmit circuitry may include transmit decoders $105_1 \ldots 105_N$ coupled to respective pulsing circuits $103_1 \ldots 103_N$. The pulsing circuits $103_1 \ldots 103_N$ may control the respective ultrasonic transducers $101_1 \ldots 101_N$ to emit ultrasound signals.

Aspects of the present application relate to pulsing circuits $103_1 \ldots 103_N$. In some embodiments, pulsing circuits $103_1 \ldots 103_N$ may be configured to generate bipolar pulses. In some embodiments, pulsing circuits $103_1 \ldots 103_N$ may be configured to generate multi-level pulses. As will be described further below, pulsing circuits $103_1 \ldots 103_N$ may include pulsers plus additional circuitry in some embodiments. In some embodiments, the pulsing circuits $103_1 \ldots 103_N$ may include pulsers and feedback circuitry.

The receive circuitry of the circuitry channels $102_1 \ldots 102_N$ may receive the electrical signals output from respective capacitive ultrasonic transducers $101_1 \ldots 101_N$. In the illustrated example, each circuitry channel $102_1 \ldots 102_N$ includes a respective receive switch $107_1 \ldots 107_N$ and a receiving circuit $109_1 \ldots 109_N$. The receive switches $107_1 \ldots 107_N$ may be controlled to activate/deactivate readout of an electrical signal from a given ultrasonic transducer $101_1 \ldots 101_N$. The receiving circuits $109_1 \ldots 109_N$ may comprise current-to-voltage converters. The current-to-voltage converters may comprise trans-impedance amplifiers (TIAs), and for that reason the receiving circuits $109_1 \ldots 109_N$ are illustrated as TIAs, although additional and/or alternative circuitry may constitute the receiving circuits.

Aspects of the present application relate to receive switches $107_1 \ldots 107_N$. In some embodiments, receive switches $107_1 \ldots 107_N$ may comprise symmetric switches configured to block voltage spikes exhibiting positive and/or negative voltages. Receive switches $107_1 \ldots 107_N$ may be configured to form an open circuit to electrically decouple the receiving circuitry from the transmitting circuitry and from the capacitive ultrasonic transducer during a transmit mode. Receive switches $107_1 \ldots 107_N$ may be further configured to form a short circuit to electrically couple the receive circuitry to the capacitive ultrasonic transducer during a receive mode.

Ultrasound device 100 may further comprise ADC 111. ADC 111 may be configured to digitize the signals received by capacitive ultrasonic transducers $101_1 \ldots 101_N$. The digitization of the various received signals may be performed in series or in parallel. While a single ADC is illustrated, and thus is shown as being shared by multiple circuitry channels, alternative embodiments provide for one ADC per circuitry channel.

While FIG. 1 illustrates a number of components as part of a circuit of an ultrasound device, it should be appreciated that the various aspects described herein are not limited to the exact components or configuration of components illustrated.

The components of FIG. 1 may be located on a single substrate or on different substrates. When located on a single substrate, the substrate may be a semiconductor substrate as an example, such as a silicon substrate, and components may be monolithically integrated thereon. When the illustrated components are not on the same substrate, the capacitive ultrasonic transducers $101_1 \ldots 101_N$ may be on a first substrate and the remaining illustrated components may be on a second substrate, as an example. As a further alternative, the ultrasonic transducers and some of the illustrated circuitry may be on the same substrate, while other circuitry components may be on a different substrate. When multiple substrates are used, they may be semiconductor substrates, such as silicon substrates.

According to an embodiment, the components of FIG. 1 form part of an ultrasound probe. The ultrasound probe may be handheld. In some embodiments, the components of FIG. 1 form part of an ultrasound patch configured to be worn by a patient.

Figure 2:
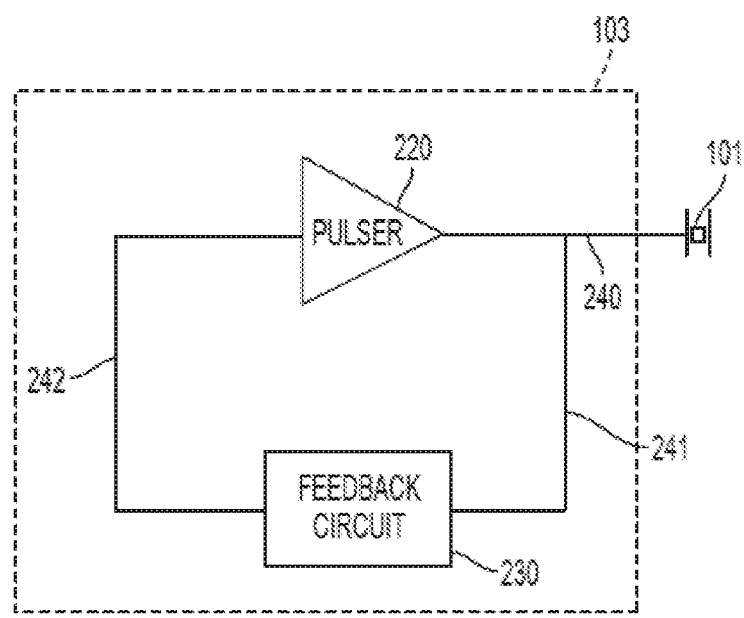
FIG. 2 is a block diagram illustrating a pulsing circuit coupled to a capacitive ultrasonic transducer, according to a non-limiting embodiment of the present application.

FIG. 2 illustrates an example of a pulsing circuit 103 which may serve as any of the pulsing circuits $103_1 \ldots 103_N$ of FIG. 1, according to some non-limiting embodiments. In some embodiments, pulsing circuit 103 may comprise puller 220 and feedback circuit 230. Pulsing circuit 103 may have an output terminal electrically connected to capacitive ultrasonic transducer 101, and may be configured to provide an input signal 240 to capacitive ultrasonic transducer 101. In some embodiments, pulser 220 may be configured to generate bipolar pulses, that may assume positive and/or negative values in addition to zero. By generating bipolar pulses, pulser 220 can diminish, or suppress, any DC component associated with the pulses. As noted previously, transmitting pulses having DC components may degrade the quality of the image produced by ultrasound device 100. Accordingly, compared to the passband component, DC components may attenuate significantly less while propagating through the medium being imaged. Consequently, the receiving circuit may receive a signal having a DC component that is significantly greater than the passband component. As a result, the receiving circuit may saturate thus limiting the dynamic range of the image.

In some embodiments, the feedback circuit may be configured to control the pulser to generate multi-level pulses. Multi-level pulses of the type described herein can assume any value selected from among a set of selectable values, where the set may comprise at least three values and in at least some embodiments may include four or more values (e.g., between 3 and 30 values, between 4 and 20 values, between 4 and 10 values, or any number within those ranges). The use of multi-level pulses may enable the optimization of the pulse's envelope to maximize a parameter of the ultrasound image being formed. For example, the envelope of the pulses may be engineered to maximize image contrast. In particular, by using time-domain apodization, the resulting frequency content of the pulses may exhibit a large main-lobe and suppressed side-lobes, thus increasing imaging resolution. Time-domain apodization requires pulses exhibiting as many voltage levels as possible to produce nearly-continuous window functions. However, the generation of pulses having a large number of levels can require complex pulsing circuits. Therefore the number of levels should be chosen to maximize the ability to perform time-domain apodization while keeping the pulsing circuits relatively simple and compact. In some embodiments, pulser 220 may be configured to generate multi-level pulses having between 3 and 30 levels, between 5 and 10 levels, or between any suitable value or range of values.

The use of multi-level pulses may also enable space-domain apodization. To perform space-domain apodization the various capacitive ultrasonic transducers would have to be driven with input signals having space-dependent amplitudes. Provision of input signals having space-dependent amplitudes may be facilitated by having access to a plurality of reference voltages.

In some embodiments, feedback circuit 230 may be configured to facilitate multi-level pulse generation. In particular, feedback circuit 230 may be configured to provide a plurality of reference voltages. As noted previously, the use of feedback circuits of the type described herein may facilitate the design of multi-level pulsers without resorting to multiple supply voltages. In some embodiments it may be undesirable to include multiple supply voltages, which may lead to sizeable ultrasound probes that may be difficult to fit in a handheld form factor. Contrarily, feedback circuits of the type described herein may provide compact circuitry to generate reference voltages and may be easily included in handheld ultrasound probes.

The output terminal of feedback circuit 230 may be electrically coupled to the input terminal of pulser 220. The input terminal of feedback circuit 230 may be electrically coupled to the output terminal of pulser 220. The input terminal of feedback circuit 230 may be configured to receive a detection signal 241 representing input signal 240. In some embodiments, input signal 240 and detection signal 241 are voltages. In some embodiments, detection signal 241 may be derived from input signal 240. In some embodiments, detection signal 241 may be proportional to input signal 240. Feedback circuit 230 may compare detection signal 241 to a threshold voltage. In some embodiments, said threshold voltage may be selected from among a set of selectable threshold voltages.

Based on the outcome of the comparison, feedback circuit 230 may provide a control signal 242 to the input terminal of pulser 220. In some embodiments, feedback circuit 230 may be configured to determine whether detection signal 241 is greater than, less than or equal to a threshold voltage. In some embodiments, feedback circuit 230 may be configured to determine whether detection signal 241 is within a range of the threshold voltage, such as within 10% of the threshold voltage, within 5% of the threshold voltage, or within any suitable range. Based on the value of detection signal 241 relative to the threshold voltage, feedback circuit 230 may control pulser 220 to hold the present value of input signal 240 or to vary input signal 240. By way of example and not limitation, if the value of detection signal 241 is less than the threshold voltage, feedback circuit 230 may control pulser 220 to increase the value of input signal 240 until detection signal 241 is equal to, or within a range of, the threshold voltage. If the value of detection signal 241 is greater than the threshold voltage, feedback circuit 230 may control pulser 220 to decrease the value of input signal 240 until detection signal 241 is equal to, or within a range of, the threshold voltage.

In some embodiments, the capacitance associated with capacitive ultrasonic transducer 101 may retain an electric charge to maintain a constant voltage across its terminals when detection signal 241 has reached the selected threshold voltage. When detection signal 241 is less than the threshold voltage, pulser 220 may be controlled to charge the capacitance associated with capacitive ultrasonic transducer 101, thus increasing input signal 240. When detection signal 241 is greater than the threshold voltage, pulser 220 may be controlled to discharge, or negatively charge, the capacitance associated with capacitive ultrasonic transducer 101, thus decreasing input signal 240.

In some embodiments, feedback circuit 230 may control pulser 220 asynchronously. Accordingly, control signal 242, input signal 240 and detection signal 241 may be allowed to vary at any moment in time. In some embodiments, pulsing circuit 100 may be timed by a clock signal. However, control signal 242 may still be allowed to vary during periods of time that are not defined by the clock signal.

In some embodiments, capacitive ultrasonic transducer 101 may be coupled to bias circuitry (not shown) and may be configured to receive a bias voltage having an absolute value that is greater than zero. The bias voltage may have an absolute value that is between 10V and 100V, between 30V and 80V, or between any suitable values or range of values. In some embodiments, biasing capacitive ultrasonic transducers may lead to responses exhibiting increased degrees of linearity.

Figure 3:
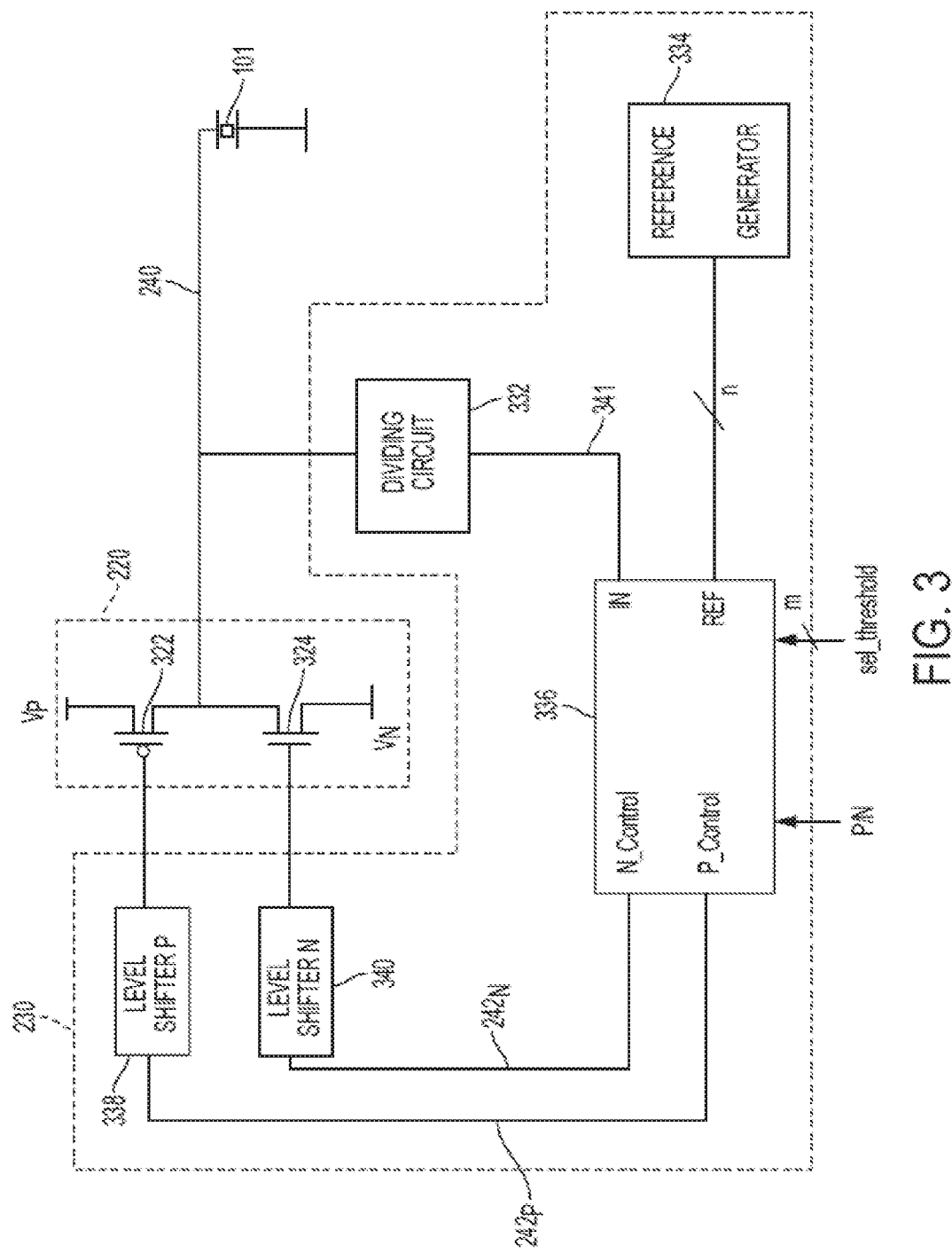
FIG. 3 is a block diagram illustrating a pulsing circuit comprising a pulser and a feedback circuit, according to a non-limiting embodiment of the present application.

FIG. 3 is a non-limiting detailed implementation of the pulsing circuit of FIG. 2. In some embodiments, pulser 220 may comprise two transistors, such as 322 and 324. However pulser 220 is not limited in this respect, and any suitable number of transistors may be used. The transistors may comprise metal-oxide-semiconductor field effect transistors (MOSFETs), junction field effect transistors (JFETs), bipolar junction transistors (BJTs), metal-semiconductor field effect transistors (MESFETs), insulated gate field effect transistors (IGFETs), laterally diffused metal-oxide-semiconductor transistors (LDMOS), or any suitable combination thereof. Pulser 220 may comprise transistor 322 and transistor 324. Transistor 322 may have one type of conductivity that is different from the type of conductivity of transistor 324. For example, transistor 322 may have a conductivity that is based on drift currents sustained by holes moving under the effect of an electric field. Transistor 324 may have a conductivity that is based on drift currents sustained by electrons moving under the effect of an electric field. In some embodiments, transistor 324 may be an nMOSFET and transistor 322 may be a pMOSFET. The transistors may be configured such that the drain of nMOS transistor 324 is connected to the drain of pMOS transistor 324. The drains may be further connected to a terminal of capacitive ultrasonic transducer 101. The source of nMOS transistor 324 may be connected to a supply voltage $V_N$. In some embodiments, $V_N$ may be less than zero. $V_N$ may be between −100V and −1V, between −50V and −20V, or between any suitable values or range of values. The source of pMOS transistor 322 may be connected to a supply voltage $V_P$. In some embodiments, $V_P$ may be greater than zero. $V_P$ may be between 1V and 100V, between 20V and 50V, or between any suitable values or range of values. The voltages provided to the gates of transistors 322 and 324 may be generated by feedback circuit 230 of FIG. 2.

In some embodiments, feedback circuit 230 may comprise controller 336, dividing circuit 332 and reference generator 334. In some embodiments, feedback circuit 230 may further comprise level shifter 338 and level shifter 340. Dividing circuit 332 may be configured to receive the voltage corresponding to input signal 240 and to output detection signal 341. Dividing circuit 332 may be configured to provide a detection signal 341 that is proportional to input signal 240. Detection signal 341 may be provided to controller 336 through the input terminal labelled "In".

Reference generator 334 may be configured to provide a set of selectable threshold voltages to the terminal labelled "Ref" of controller 336. In some embodiments, reference generator 334 is connected to controller 336 through n connectors, and is configured to provide n threshold voltages through corresponding connectors, where n may assume any suitable value greater than two. The threshold voltages may be equal to, greater, or less than zero.

In some embodiments, feedback circuit 230 may be digitally controlled, and controller 336 may comprise a digital controller. Controller 336 may be configured to control pulser 220 to hold, increase or decrease the voltage corresponding to input signal 240 based on a comparison of detection signal 341 with a threshold voltage, selected from among the n threshold voltages. Controller 336 may select a threshold voltage from the n threshold voltages provided by reference generator 334. The threshold voltage may be digitally selected through signal sel_threshold. Signal sel_threshold may comprise m bits, where m is such that n is equal to, or less than, $2^m$. Each bit combination may select one threshold voltage from the n threshold voltages. By way of example and not limitation, a sel_threshold sequence equal to 000 may select the least of 8 threshold voltages, and a sel_threshold sequence equal to 111 may select the largest of 8 threshold voltages. Furthermore, signal sel_threshold may be varied asynchronously.

In some embodiments, dividing circuit 332 may provide a detection signal 341 that is proportional to input signal 240 by a scaling factor. In such embodiments, reference generator 334 may be configured to provide a set of threshold voltages that are scaled to input signal 240 by the same scaling factor. Consequently, detection signal 341 may be directly compared to the selected threshold voltage without having to further scale one of the two signals.

In some embodiments, signal p/n may be used to control the status of transistors 322 and 324. In some embodiments, p/n may be a single bit signal. Signal p/n may be set to "p" to activate transistor 322, or to "n" to activate transistor 324. However any suitable number of bits configured to control the status of transistors 322 and 324 may also be used. The value of the single bit may cause either transistor 322 or transistor 324 to turn into a conductive state, whether in linear or saturation mode. In such embodiment, only one transistor at a time may be set to a conductive state.

Based on the value of sel_threshold and p/n, controller 336 may output control signals $242_P$ and $242_N$, through the output terminals labelled "N_control" and "P_control", Together, control signals $242_P$ and $242_N$, may represent control signal 242 illustrated in FIG. 2. Signal $242_P$ may comprise a single bit, in some embodiments, configured to control the state of pMOS transistor 322. Signal $242_N$ may comprise a single bit, in some embodiments, configured to control the state of nMOS transistor 324. The two transistors may be allowed to be in a cutoff state at the same time.

In some embodiments, control signals $242_P$ and $242_N$ may directly drive the gates of transistors 322 and 324 respectively. In other embodiments, as shown in FIG. 3, control signals $242_P$ and $242_N$ may be coupled to the input terminals of level shifter 338 and level shifter 340, respectively. The output terminals of level shifter 338 and level shifter 340 may be coupled to the gates of transistors 322 and 324 respectively. Level shifters 338 and level shifter 340 may be configured to adapt the voltages generated by controller 336 to voltages compatible to transistors 322 and 324 to drive the transistors into their cutoff or conductive state, based on signals $242_P$ and $242_N$.

When detection signal 341 is less than the selected threshold voltage, controller 336 may be configured to output control signals $242_P$ and $242_N$ with values suitable to turn pMOS transistor 322 into a conductive state and nMOS 324 transistor into a cutoff state. In this case, an electric current flowing from voltage supply $V_P$ to capacitive ultrasonic transducer 101 may charge capacitive ultrasonic transducer 101 until detection signal 341 reaches the selected threshold voltage, or a predetermined range of the selected threshold voltage.

When detection signal 341 is greater than the selected threshold voltage, controller 336 may be configured to output control signals $242_P$ and $242_N$ with values suitable to turn nMOS transistor 324 into a conductive state and pMOS transistor 322 into a cutoff state. In this case, an electric current flowing from capacitive ultrasonic transducer 101 to voltage supply $V_N$ may discharge, or negatively charge, capacitive ultrasonic transducer 101 until detection signal 341 reaches the selected threshold voltage, or a predetermined range of the selected threshold voltage.

When detection signal 241 is equal or within a predetermined range of the selected threshold voltage, pMOS transistor 322 and mMOS transistor 324 may be controlled through signals $242_P$ and $242_N$ to both turn into a cutoff state. In this case, no electric current would flow to or from capacitive ultrasonic transducer 101. Consequently, capacitive ultrasonic transducer 101 may retain an electric charge, thus holding the target voltage corresponding to the selected threshold voltage across its terminals.

Because, as described above, in at least some embodiments it may be desirable for the ultrasound transducers 101 to hold their charge, in such embodiments the ultrasound transducers may be capacitive. By contrast, the use of resistive ultrasound transducers may not operate properly in such situations.

While controller 336 may be configured to control pulser 220 based on the signals p/n and sel_threshold in the non-limiting embodiment described in connection with FIG. 3, pulsing circuit 103 is not limited in this respect. Accordingly, any signal, or combination of signals, configured to control pulser 220 to hold, increase or decrease input signal 240 until a threshold voltage, or a range of the threshold voltage, is reached, may also be employed.

Figure 4:
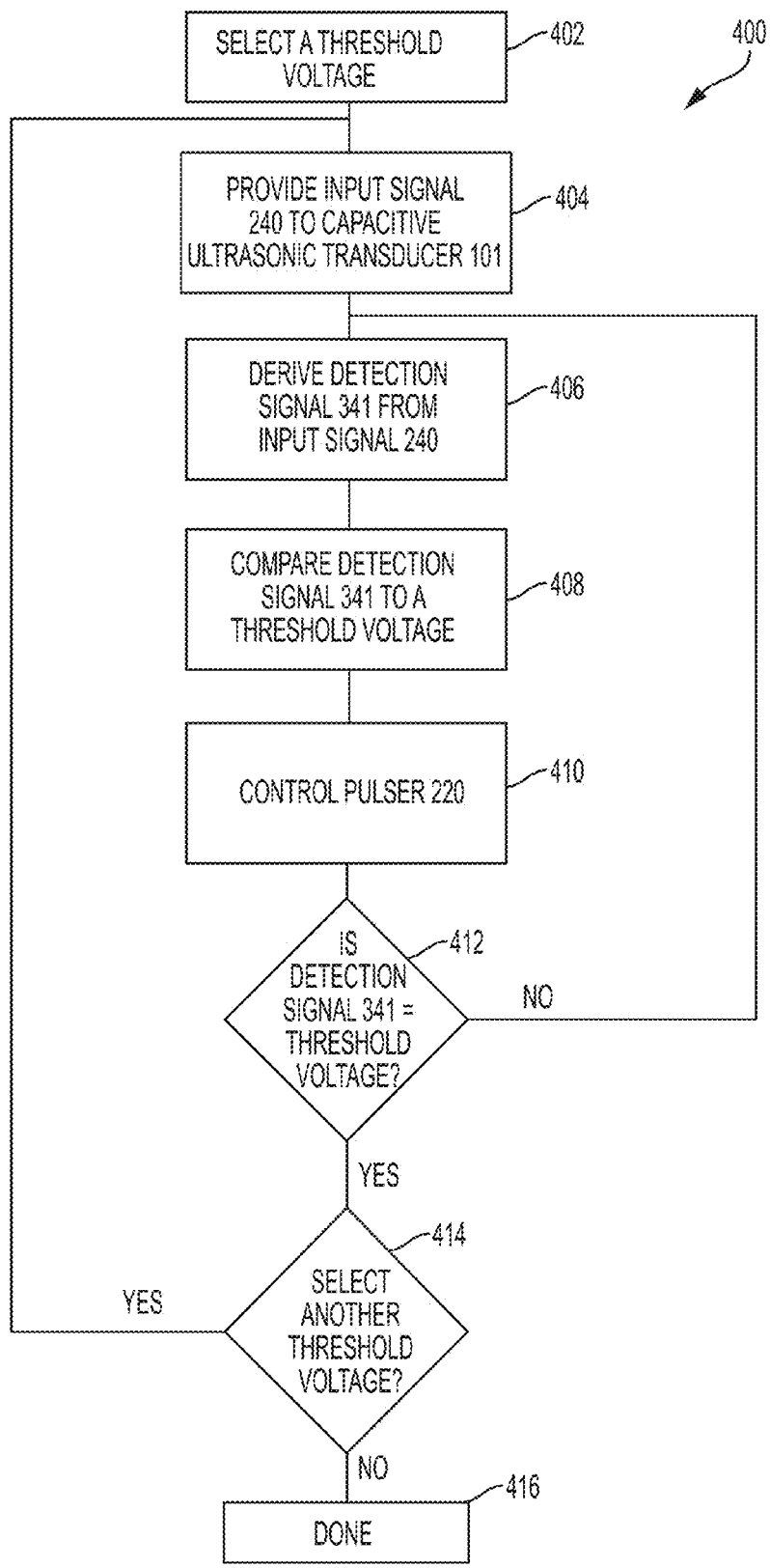
FIG. 4 is a block diagram illustrating the acts of a method to operate a pulsing circuit coupled to a capacitive ultrasonic transducer, according to a non-limiting embodiment of the present application.

FIG. 4 illustrates a method to operate a pulsing circuit to drive a capacitive ultrasonic device, according to some non-limiting embodiments. The method of FIG. 4 may be performed in connection with the pulsing circuit of FIG. 2 or the pulsing circuit of FIG. 3. Method 400 starts at act 402, where a threshold voltage may be selected from among a set of n selectable threshold voltages, where n may assume any suitable value greater than two. In some embodiments the threshold voltage may be selected through a digital signal having m bits, where n is equal to, or less than, $2^m$.

Method 400 continues to act 404, where an input signal, such as input signal 240, may be provided by pulser 220 to capacitive ultrasonic transducer 101. According to one aspect of the present application, pulser 220 may be configured to provide a bipolar input signal, which may exhibit positive and/or negative voltages. Bipolar input signals of the type described herein may lead to echo signals that do not saturate the receiving circuit of the ultrasound device.

According to another aspect of the present application, pulser 220 may be configured to provide a multi-level pulse, which may exhibit values selected from among multiple selectable values. Pulsing circuits capable of generating multi-level pulses may facilitate time-domain and space-domain apodization, which may lead to enhanced image contrast. The generation of multi-level pulses of the type described herein may be facilitated by feedback circuits designed to provide a threshold voltage selected from a set of threshold voltages, without resorting to additional voltage supply circuits that may render handheld ultrasound probes more sizeable.

At act 406, a detection signal, such as detection signal 341, may be derived from input signal 240. Detection signal 341 may represent input signal 240. Accordingly, detection signal 341 may be equal, or proportional, to input signal 240.

At act 408, detection signal 341 may be compared to the threshold voltage selected at act 402. In some embodiments detection signal 341 is proportional to input signal 240 by a scaling factor. In such embodiments, the threshold voltage may be scaled to input signal 240 by the same scaling factor. As a result of the comparison, detection signal 341 may be equal to, greater than, or less than the threshold voltage.

At act 410, based on the result of the comparison performed at act 408, a control signal 242 may be provided to pulser 220 to control input signal 240. The control signal may be provided by feedback circuit 230. Feedback circuit 230 may be controlled digitally. At act 412, if detection signal 341 is less than the selected threshold voltage, control signal 242 may control pulser 220 to increase the voltage corresponding to input signal 240. In some embodiments, control signal 242 may turn pMOS transistor 322 into a conductive state to charge the capacitance associated to capacitive ultrasonic transducer 101.

At act 412, if detection signal 341 is greater than the selected threshold voltage, control signal 242 may control pulser 220 to decrease the voltage corresponding to input signal 240. In some embodiments, control signal 242 may turn nMOS transistor 324 into a conductive state to discharge, or negatively charge, the capacitance associated to capacitive ultrasonic transducer 101.

In either case, method 400 may return back to act 406 and method 400 may repeat until detection signal 341 is equal or within a predefined range of the selected threshold voltage.

At act 412, if detection signal 341 is found to be equal or within a predefined range of the selected threshold voltage, control signal 242 may control pulser 220 to hold the current value of input signal 240. In some embodiments, control signal 242 may turn nMOS transistor 324 and pMOS transistor 322 into a cutoff state to allow the capacitance associated with capacitive ultrasonic transducer 101 to retain the current electric charge. The predefined range may be defined as 10% within the selected threshold voltage, 5% within the selected threshold voltage, or within any suitable range.

Once input signal 240 has reached the voltage corresponding to the threshold voltage, another threshold voltage may be selected from among the n selectable threshold voltages at act 414. If another threshold voltage is selected at act 414, method 400 may repeat from act 404 for the newly selected threshold voltage. The selection of the new threshold voltage may be performed asynchronously. Otherwise, if no new threshold voltage is selected, method 400 may end at act 416.

Figure 5A:
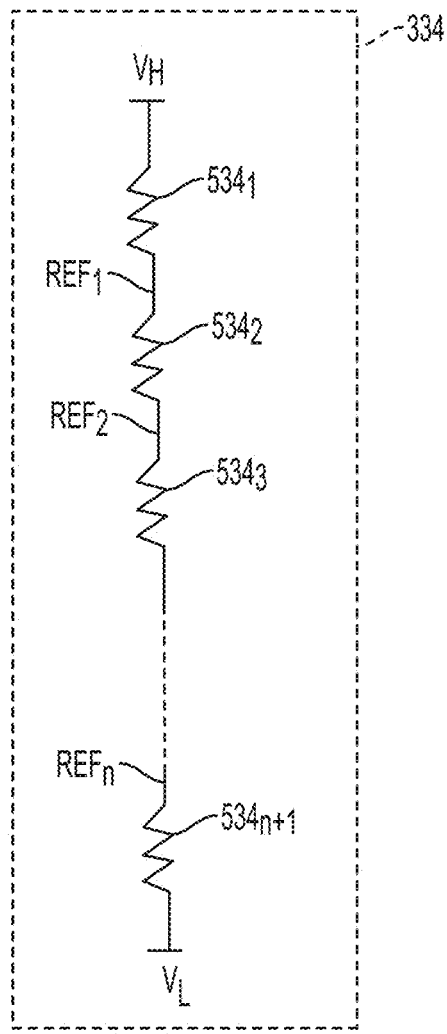
FIG. 5A is a circuit diagram illustrating a resistive ladder configured to generate a plurality of threshold voltages, according to a non-limiting embodiment of the present application.

FIG. 5A illustrates the circuit diagram of the reference generator of FIG. 3, according to some non-limiting embodiments. Reference generator 334 may comprise a resistive ladder, configured to generate n threshold voltages $ref_1 \ldots ref_n$, where n may assume any value greater than two. The resistive ladder may comprise n+1 resistors $534_1 \ldots 534_{n+1}$ connected in series, in some embodiments. Resistor $534_1$ may be coupled to supply voltage $V_H$. Supply voltage $V_H$ may be equal to supply voltage $V_P$, shown in FIG. 3. Resistor $534_{n+1}$ may be coupled to supply voltage $V_L$. Supply voltage $V_L$ may equal supply voltage $V_N$, shown in FIG. 3. In some embodiments, the n+1 resistors may all have equal resistances to divide the voltage range corresponding to $V_H$-$V_L$ into n equal segments. In other embodiments, resistors $534_2 \ldots 534_{n+1}$ may have resistances equal to R, while resistor $534_1$ may have a resistance equal to xR, where x may assume any value between 0.01 and 100. However, other values are also possible. In such embodiments, a scaled voltage range proportional to $V_H$-$V_L$ may be divided into n equal segments.

Figure 5B:
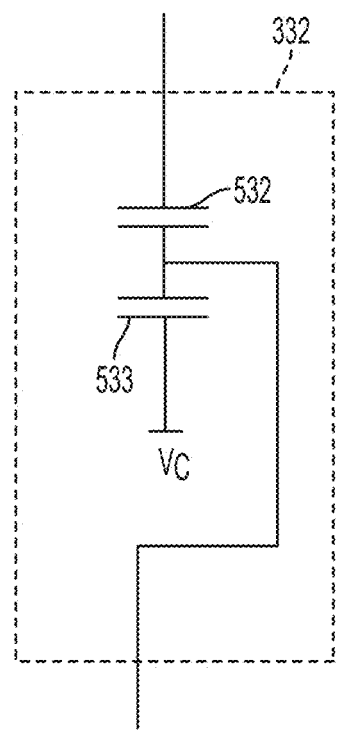
FIG. 5B is a circuit diagram illustrating a dividing circuit configured to generate a detection signal, according to a non-limiting embodiment of the present application.

FIG. 5B illustrates the circuit diagram of the dividing circuit of FIG. 3, according to some non-limiting embodiments. The dividing circuit may comprise a capacitive divider, configured to generate a detection signal 341 that is proportional to input signal 240. The capacitive divider may comprise capacitor 532 and capacitor 533. Capacitor 532 may have one terminal coupled to the output of pulser 220 and one terminal coupled to an input of controller 336. In some embodiments, capacitor 532 may be configured to receive input signal 240 generated from by pulser 220. Capacitor 533 may have one terminal coupled to the same input of controller 336 and one terminal coupled to supply voltage $V_C$. In some embodiments, capacitor 336 may be configured to receive a scaled version of input signal 240. In some embodiments, supply voltage $V_C$ may be equal to supply voltage $V_N$ shown in FIG. 3. The capacitance of capacitors 532 and 533 may be configured to scale detection signal 341 by the same scaling factor by which the threshold voltages of FIG. 5A are scaled. In such embodiments, detection signal 341 may be directly compared to a threshold voltage selected from among the n threshold voltage without having to scale any of the two signals first.

Figure 6A:
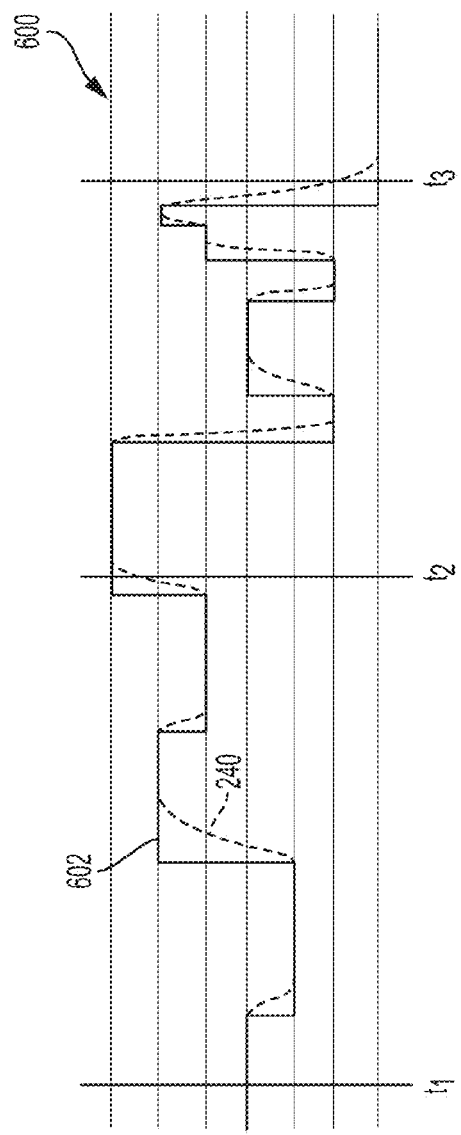
FIG. 6A illustrates a timing diagram showing an example signal provided by the pulsing circuit to the capacitive ultrasonic transducer, according to a non-limiting embodiment of the present application.

FIG. 6A illustrates a timing diagram showing an example signal provided by the pulsing circuit to the capacitive ultrasonic transducer, according to a non-limiting embodiment of the present application. In particular, timing diagram 600 illustrates an exemplary target signal 602 and an exemplary input signal 240. In the non-limiting embodiment presented in connection with FIG. 6A, a threshold voltage may be selected from among seven threshold voltages. Target signal 602 represents the signal to be followed by input signal 240. When input signal 240 is equal to target signal 602, for example at $t_1$, then detection signal 341 is equal to the current threshold voltage. In this case, feedback circuit 230 may control pulser 220 to keep input voltage 240 constant at the current value. When input voltage 240 is less than target voltage 602, for example at $t_2$, feedback circuit 230 may control pulser 220 to increase input voltage 240 until the current target voltage is reached. When input voltage 240 is greater than target voltage 602, for example at $t_3$, feedback circuit 230 may control pulser 220 to decrease input voltage 240 until the current target voltage is reached. In some embodiments, target signal 602 may be varied asynchronously. Consequently the duration of each segment of target voltage 602 may be set independently from the duration of the other segments.

In some embodiments, pulsing circuit 103 may be configured to generate an input signal 240 having a DC component that is greater than zero. The extent of the DC component may be chosen to bias the receiving circuit without letting it reach saturation.

In some embodiments, input signal 240 may overshoot target signal 602 (not shown). To mitigate the occurrence of such an overshoot, feedback circuit 230 may be configured to skew the threshold voltage. In some embodiments, the threshold voltage may be skewed by adding (or subtracting) a voltage offset to the threshold voltage. For example, if the desired output voltage is x volts, the threshold voltage may be set to y volts, such that the difference between x and y is equal to the overshooting voltage. In some embodiments, the threshold voltage may be skewed through a non-uniform resistive ladder.

Figure 6B:
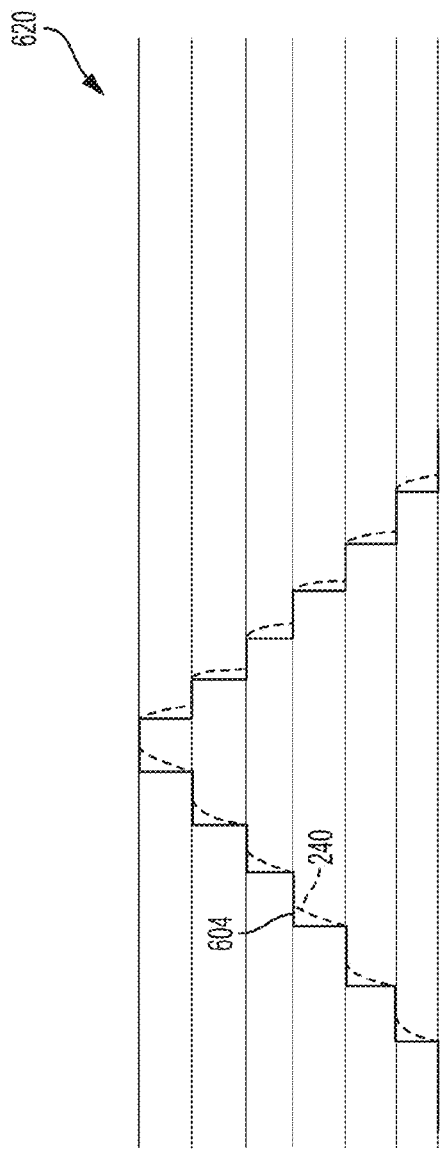
FIG. 6B illustrates a timing diagram showing an apodized signal provided by the pulsing circuit to the capacitive ultrasonic transducer, according to a non-limiting embodiment of the present application.

FIG. 6B illustrates a timing diagram showing an apodized signal provided by the pulsing circuit to the capacitive ultrasonic transducer, according to a non-limiting embodiment of the present application. In particular, timing diagram 620 illustrates an apodized target signal 604 and an apodized input signal 240. Feedback circuit 230 may be configured to perform time-domain apodization of input signal 240 based on a Gaussian window, a Hamming window, a flat top window, a cosine window, or any suitable window function. Multi-level pulses of the type described herein provide a sufficient degree of granularity to faithfully generate continuous window functions.

Figure 7:
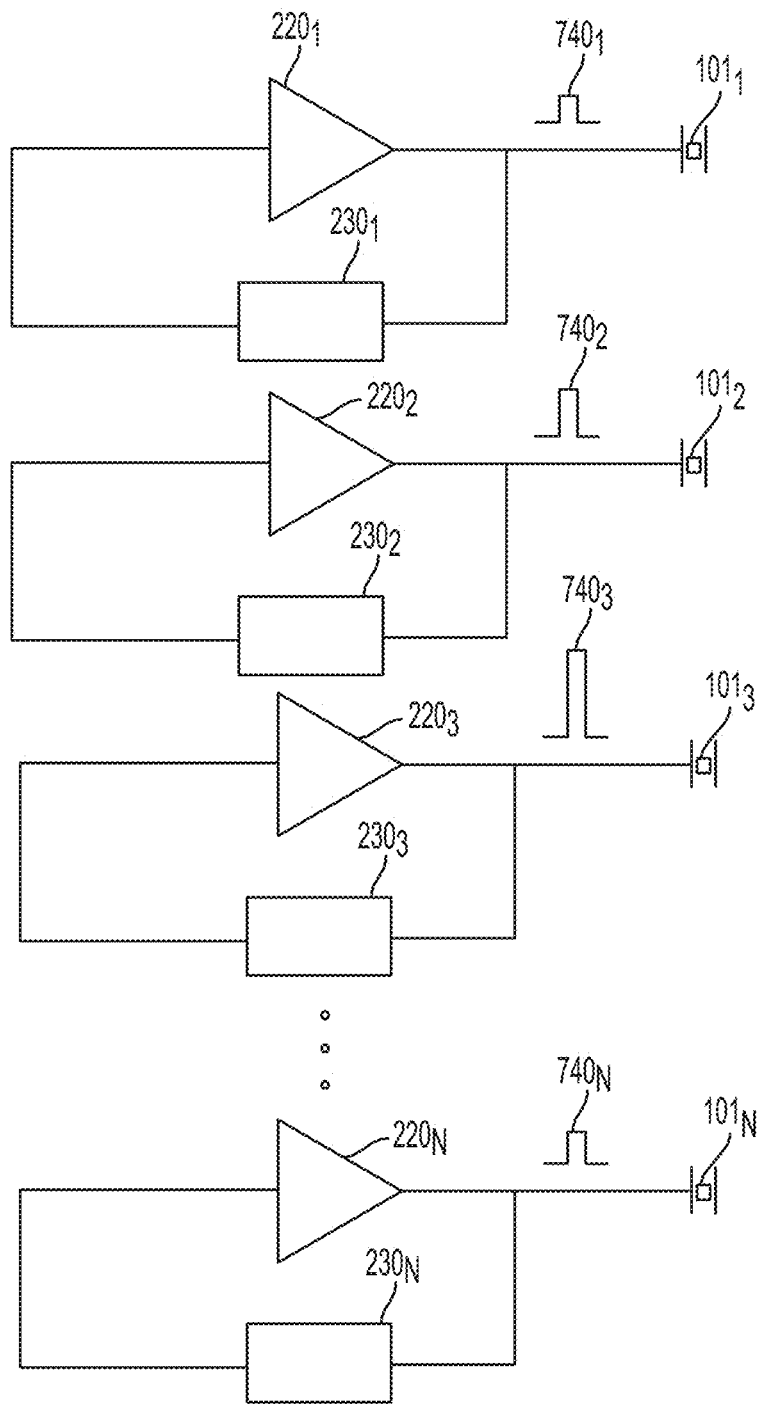
FIG. 7 is a block diagram illustrating a plurality of pulsing circuits coupled to a plurality of capacitive ultrasonic transducers, according to a non-limiting embodiment of the present application.

FIG. 7 is a block diagram illustrating a plurality of pulsing circuits coupled to a plurality of capacitive ultrasonic transducers, according to a non-limiting embodiment of the present application. In some embodiments, capacitive ultrasonic transducers $101_1$, $101_2$, $101_3$ ... $101_N$ may be disposed to form a 1D array. In other embodiments, capacitive ultrasonic transducers $101_1$ ... $101_N$ may be disposed to form a 2D array. Capacitive ultrasonic transducers $101_1$ ... $101_N$ may be coupled to the output terminal of a respective pulser among pulsers $220_1$, $220_2$, $220_3$ ... $220_N$. Feedback circuits $230_1$, $230_2$, $230_3$ ... $230_N$ may be coupled to the input terminal and to the output terminal of a respective pulser among pulsers $220_1$ ... $220_N$. In some embodiments, feedback circuits $230_1$ ... $230_N$ may be separate circuits. In other embodiments, feedback circuits $230_1$ ... $230_N$ may be part of a single circuit, configured to control pulsers $220_1$ ... $220_N$. As illustrated in FIG. 7, feedback circuits $230_1$ ... $230_N$ may control pulsers $220_1$ ... $220_N$ to generate input signal $740_1$, $740_2$, $740_3$, ... $740_N$ that exhibit amplitudes that are space-dependent. In some embodiments the feedback circuits may control the pulsers to perform space-domain apodization of the input signals. By way of example and not limitation, input signals $740_1$ ... $740_N$ may exhibit amplitudes that are larger at the center of the array and decay, following a predefined profile, towards the edge of the array. The space-domain apodization function may be a Gaussian window, a Hamming window, a flat top window, a cosine window, or any suitable window function. Space-domain apodization may be performed over one spatial dimension or two spatial dimensions. By performing space-domain apodization, the aperture of the array may be effectively varied, thus providing means to optimize the spatial profile of the emitted ultrasound wave. In some embodiments, the spatial profile may be optimized to minimize spatial side-lobes. Ultrasound devices capable of emitting spatial profiles that have minimal, or suppressed, side-lobes exhibit enhanced spatial resolution and hence increased image contrast.

In some embodiments, capacitive ultrasonic transducer 101 may be connected to transmit and receive circuitry. During transmission, the bipolar input signal generated by the pulsing circuit may inadvertently couple to the receiving circuit. The receiving circuit may comprise, in some embodiments, components that are not designed to withstand large positive and negative voltage spikes of the type generated with pulser 220. Accordingly, coupling bipolar pulses directly into the receiving circuit may have the effect of damaging one or more components.

Figure 8A:
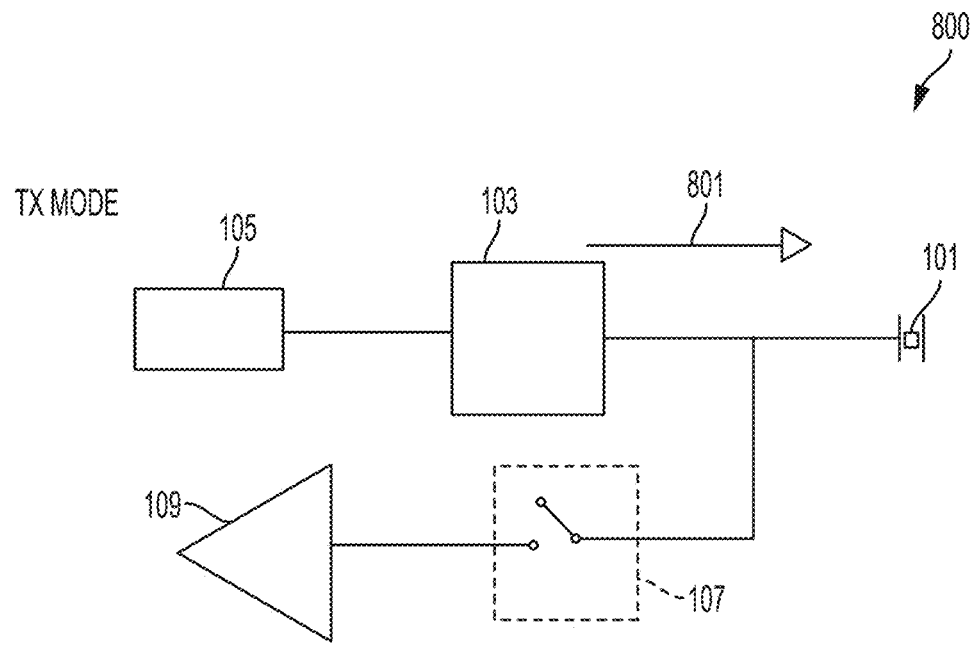
FIG. 8A is a block diagram illustrating an ultrasound device operating in transmit mode, according to a non-limiting embodiment of the present application.
Figure 8B:
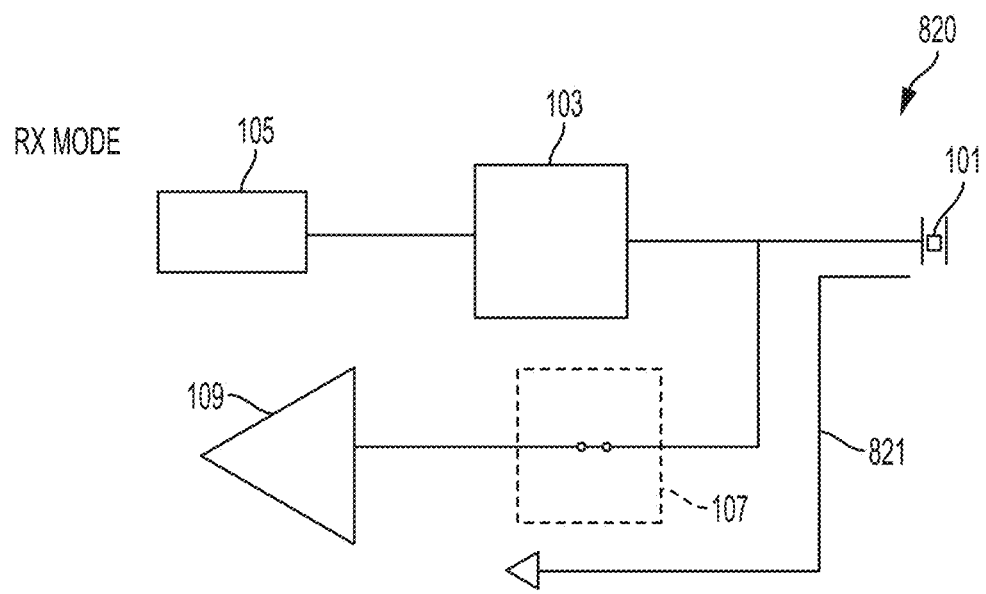
FIG. 8B is a block diagram illustrating an ultrasound device operating in receive mode, according to a non-limiting embodiment of the present application.

According to aspects of the present application, a symmetric switch configured to decouple the receiving circuit from the transmitting circuit while the bipolar pulses are being generated is provided. As used herein, a symmetric switch is a transistor-based switch which has input and output terminals of the same type. For example, the input and output terminals of the switch may both be sources, both drains, both emitters, both collectors, or other terminal types. FIG. 8A and FIG. 8B are block diagrams illustrating an ultrasound device operating in transmit mode and receive mode respectively, according to a non-limiting embodiment of the present application. Symmetric switch 107 may have an input terminal connected to the output terminal of pulsing circuits 103. In some embodiments, the input terminal of symmetric switch 107 may be connected to the output terminal of pulser 220 of pulsing circuit 103. The input terminal of symmetric switch 107 may be further connected to a terminal of capacitive ultrasonic transducer 101. In some embodiments, the input terminal of symmetric switch 107 may be coupled between the output terminal of pulser 220 and a terminal of capacitive ultrasonic transducer 101. Symmetric switch may also have an output terminal coupled to the input terminal of receiving circuit 109. In some embodiments, receiving circuit 109 comprises a current-to-voltage converter configured to convert the current generated by capacitive ultrasonic transducer 101 in response to receiving an echo signal. In some embodiments, the current-to-voltage converter may comprise a trans-impedance amplifier (TIA).

As illustrated in FIG. 8A, in transmit mode (TX mode), symmetric switch 107 may be configured to provide high impedance to decouple the pulse generated by pulsing circuit 103 from receiving circuit 109. In some embodiments, symmetric switch 107 may be configured to operate as an open circuit during transmit mode. Arrow 801 may represent the signal path corresponding to input signal 240 during transmit mode.

As illustrated in FIG. 8B, in receive mode (RX mode), symmetric switch 107 may be configured to provide low impedance to couple the pulse generated by capacitive ultrasonic transducer 101 in response to receiving an echo signal (or other received signal) to receiving circuit 109. In some embodiments, symmetric switch 107 may be configured to short-circuit receiving circuit 109 to capacitive ultrasonic transducer 101 during receive mode. In some embodiments, pulsing circuit 103 may be configured to be in a high-impedance state during receive mode. Arrow 821 may represent the signal path corresponding to the received signal during receive mode.

Figure 9:
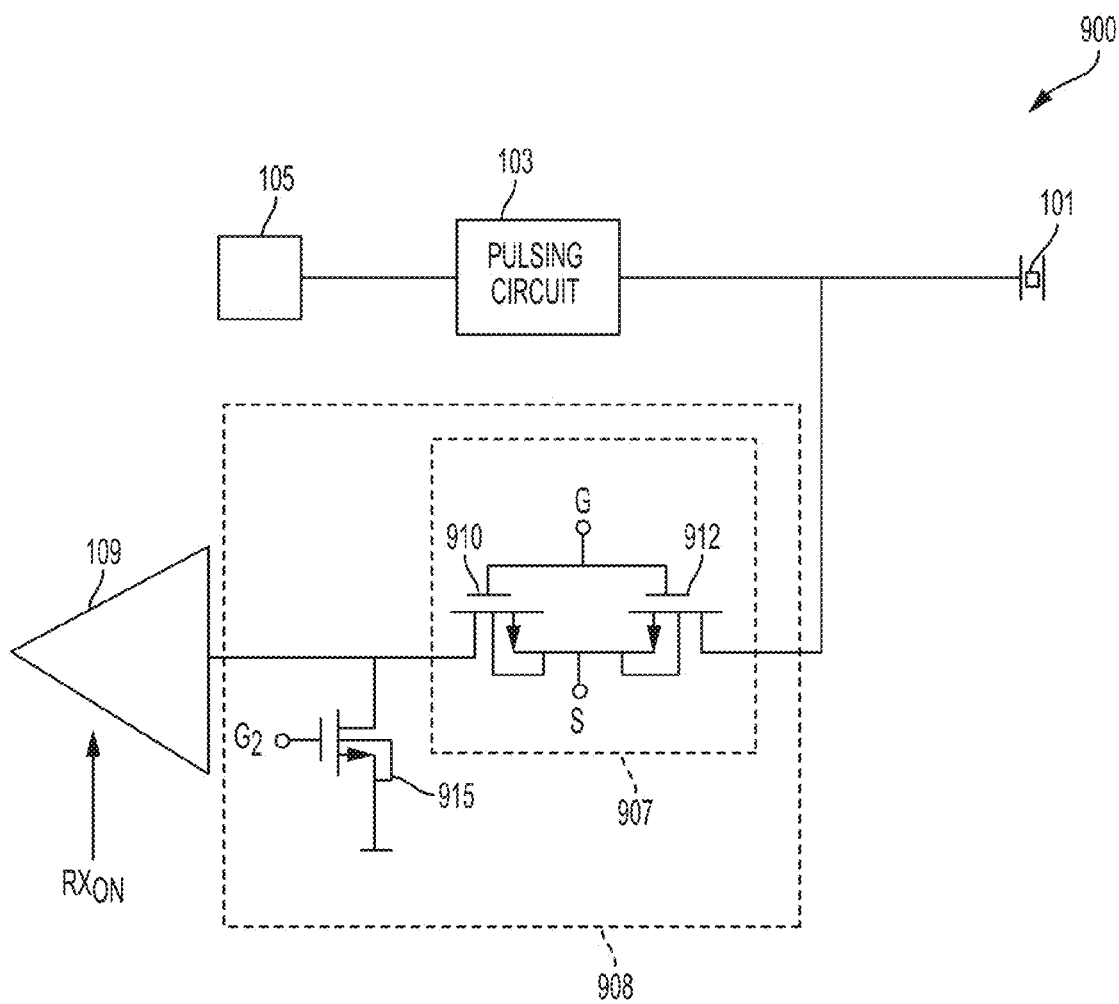
FIG. 9 is a block diagram illustrating an ultrasound device comprising a symmetric switch, according to a non-limiting embodiment of the present application.

FIG. 9 illustrates a block diagram 900 of an ultrasound device comprising a symmetric switch, according to a non-limiting embodiment of the present application. Symmetric switch 907 may be configured to block positive and negative voltages associated with the bipolar pulses generated by pulsing circuit 103, thus preventing damage to receiving circuit 109.

In some embodiments, symmetric switch 907 may comprise two transistors 910 and 912. However, symmetric switch 907 may include any suitable number of transistors configured to block bipolar pulses during transmit mode. Transistors 910 and 912 may be of any type, such as metal-oxide-semiconductor field effect transistors (MOSFETs) including nMOS or pMOS, junction field effect transistors (JFETs), bipolar junction transistors (BJTs), metal-semiconductor field effect transistors (MESFETs), insulated gate field effect transistors (IGFETs), laterally diffused metal-oxide-semiconductor transistors (LDMOS), or any suitable combination thereof. In some embodiments, both transistors 910 and 912 are nMOS. The gate of transistor 910 may be short-circuited to the gate of transistor 912. In some embodiments, a second terminal, other than the gate, of transistor 910 may be short-circuited to a second terminal, other than the gate, of transistor 912. By way of example and not limitation, the source of transistor 910 may be short-circuited to the source of transistor 912. The third terminal of transistor 912, for example, the drain, may be coupled between the output terminal of pulsing circuit 103 and a terminal of capacitive ultrasonic transducer 101. The third terminal of transistor 910, for example, the drain, may be coupled to the input terminal of receiving circuit 109. In some embodiments, the drain of transistor 910 may be short-circuited to the input terminal of receiving circuit 109. In some embodiments, the body terminal of transistor 910 may be short-circuited to the source of transistor 910 and the body terminal of transistor 912 may be short-circuited to the source of transistor 912.

In some embodiments, switching circuit 908 may be used to block bipolar pulses during transmit mode. Switching circuit 908 may comprise symmetric switch 907 and transistor 915. Transistor 915 may be any suitable type of transistor. By way of example and not limitation, transistor 915 may be an nMOS. Transistor 915 may be configured to have the drain short-circuited to the input terminal of receiving circuit 109. The source of transistor 915 may be short-circuited to a ground terminal. The body terminal of transistor 915 may be short-circuited to its source.

Figure 11:
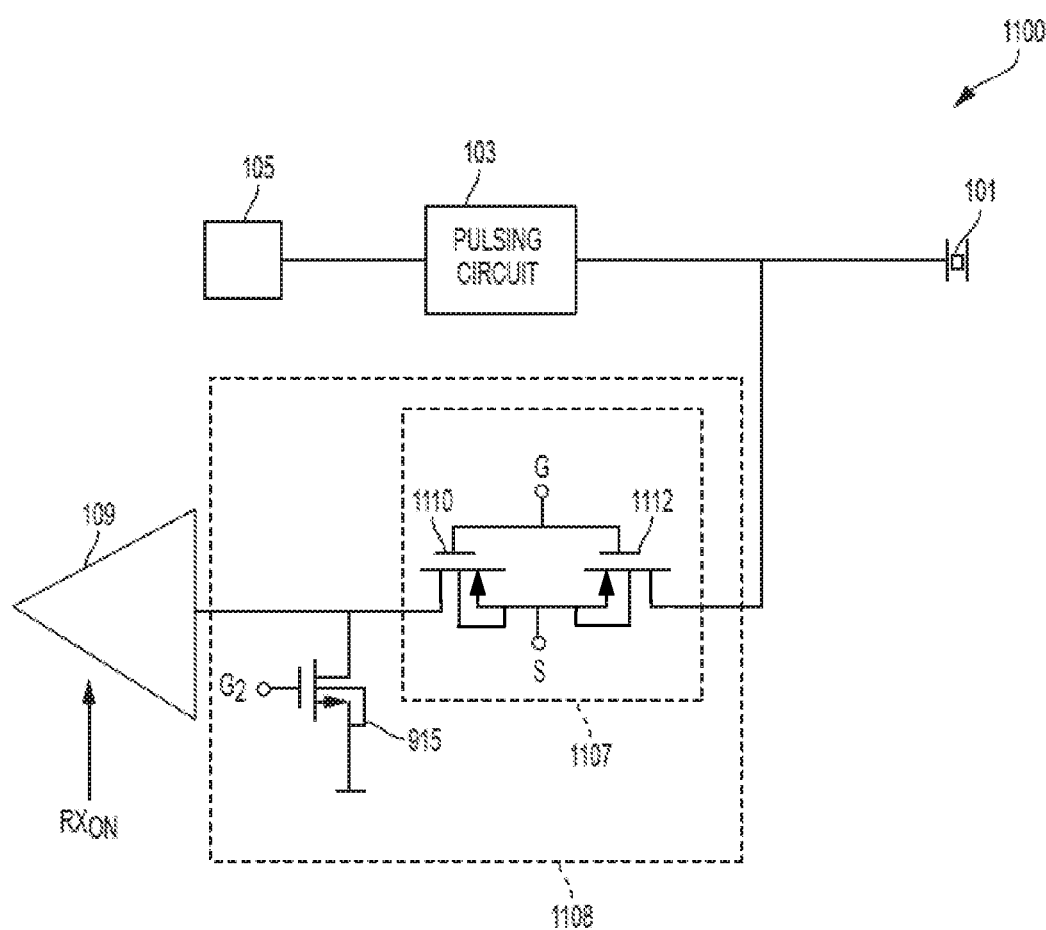
FIG. 11 is a block diagram illustrating an alternative device comprising a symmetric switch, according to a non-limiting embodiment of the present application.

In some embodiments, the symmetric switch may comprise pMOS transistors. FIG. 11 illustrates a block diagram 1100 of an ultrasonic device comprising a symmetric switch, where the symmetric switch comprises two pMOS transistors 1110 and 1112, according to a non-limiting embodiment of the present application. While FIG. 11 illustrates a symmetric switch comprising two pMOS transistors, any other suitable number of pMOS transistors may be used.

Symmetric switch 1107 may be configured such that the gate of transistor 1110 may be short-circuited to the gate of transistor 1112. In some embodiments, a second terminal, other than the gate, of transistor 1110 may be short-circuited to a second terminal, other than the gate, of transistor 1112. By way of example and not limitation, the source of transistor 1110 may be short-circuited to the source of transistor 1112. The third terminal of transistor 1112, for example, the drain, may be coupled between the output terminal of pulsing circuit 103 and a terminal of capacitive ultrasonic transducer 101. The third terminal of transistor 1110, for example, the drain, may be coupled to the input terminal of receiving circuit 109. In some embodiments, the drain of transistor 1110 may be short-circuited to the input terminal of receiving circuit 109. In some embodiments, the body terminal of transistor 1110 may be short-circuited to the source of transistor 1110 and the body terminal of transistor 1112 may be short-circuited to the source of transistor 1112. In some embodiments, switching circuit 1108 may comprise symmetric switch 1107 and transistor 915.

Figure 10:
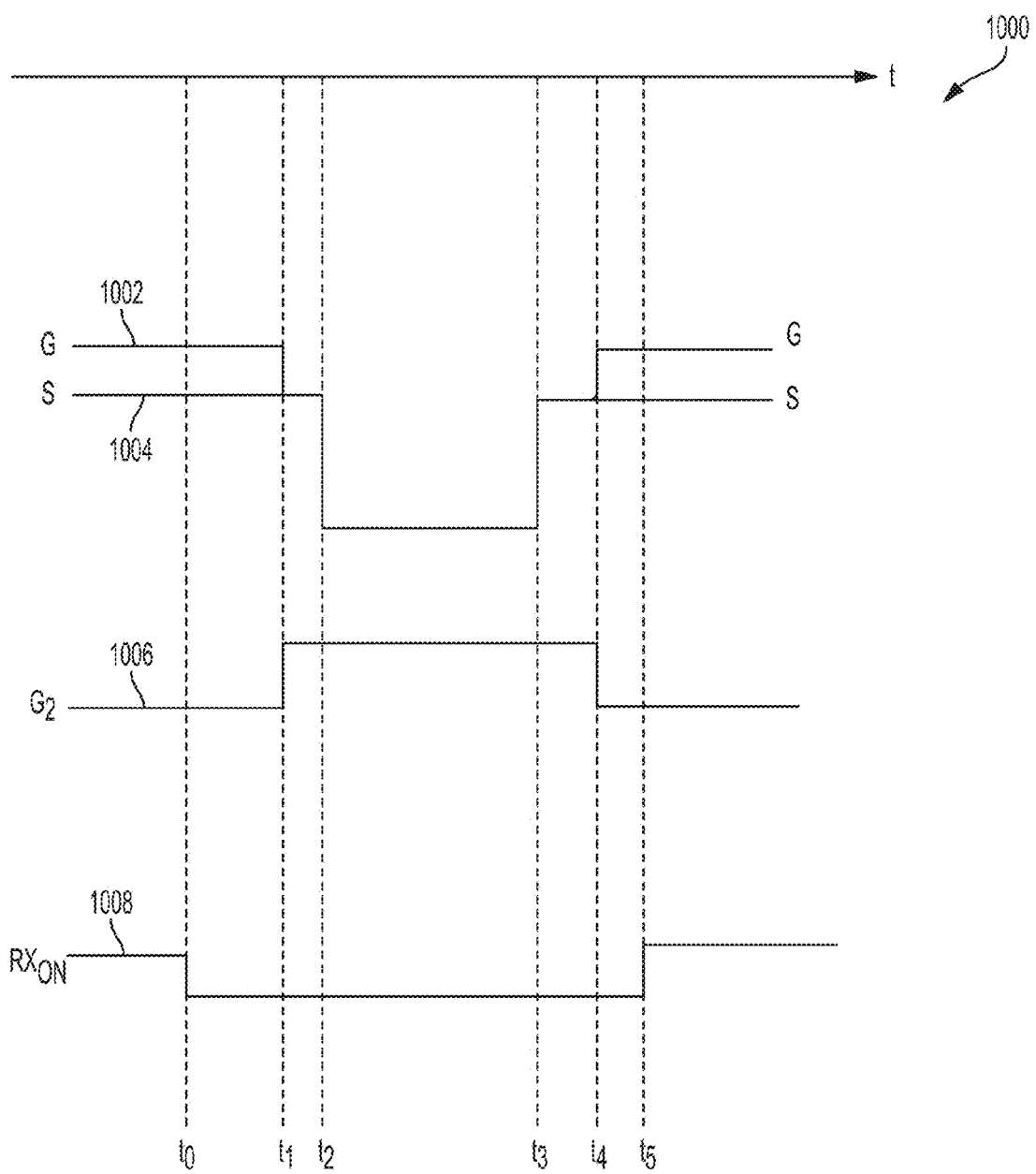
FIG. 10 illustrates a timing diagram showing control signals configured to drive the symmetric switch of FIG. 9, according to a non-limiting embodiment of the present application.

Switching circuit 908 may be controlled by any suitable type and number of control signals configured to block bipolar pulses generated by pulsing circuit 103 during transmit mode and further configured to couple capacitive ultrasonic transducer 101 to receiving circuit 109 during receive mode. By way of example and not limitation, FIG. 10 illustrates a timing diagram 1000 showing control signals configured to drive the symmetric switch of FIG. 9, according to a non-limiting embodiment of the present application. Control signal 1002 may control the gates of transistors 910 and 912 via terminal G. Control signal 1004 may control the sources of transistors 910 and 912 via terminal S. Control signal 1006 may control the gate of transistor 915 via terminal $G_2$. In some embodiments, receiving circuit 109 may be turned on and off with control signal 1008. For example, control 1008 may enable/disable the voltage supply of receiving circuit 109.

Before $t_0$, switching circuit 908 may be configured to operate in receive mode. During this period, control signal 1002 may be greater than control signal 1004. In some embodiments, both control signals 1002 and 1004 may be greater than zero. In this way, both transistors may have a gate-source voltage greater than zero and hence may be configured to conduct electric currents. Control signal 1006 may be zero or below the threshold voltage of transistor 915 to maintain transistor 915 in a cutoff state. In some embodiments, control signal 1008 may be set to a value that enables receiving circuit 109.

Between $t_0$ and $t_1$ control signal 1008 may be set to a value that disables receiving circuit 109.

Between $t_1$ and $t_2$ control signal 1002 may be set to a value equal to control signal 1004. Consequently, transistors 910 and 912 may turn into their cutoff mode. In some embodiments, control signal 1006 may be set to a value above the threshold voltage of transistor 915. Consequently, the input terminal of receiving circuit 109 may be forced to a voltage equal to zero.

Between $t_2$ and $t_3$ control signals 1002 and 1004 may be set to a negative voltage. In some embodiments, control signals 1002 and 1004 may be set to a negative voltage simultaneously. In some embodiments the negative voltage may be equal to $V_N$ shown in FIG. 3.

Between $t_3$ and $t_4$ control signals 1002 and 1004 may be set to zero or to the bias voltage of pulsing circuit 103. In some embodiments, control signals 1002 and 1004 may be set to zero or to the bias voltage of pulsing circuit 103 simultaneously.

Between $t_4$ and $t_5$ control signal 1002 may be set to a voltage such that the gate-source voltages of transistors 910 and 912 are above threshold. In some embodiments, control signal 1006 may be set to a value below the threshold voltage of transistor 915, so that the voltage associated with the input terminal of receive circuit 109 may fluctuate freely.

After $t_5$ control signal 1008 may be set to a value that enables receiving circuit 109.

In some embodiments, the receive mode may be defined by the time periods before $t_0$ and after $t_5$ and the transmit mode may be defined by the time period between $t_0$ and $t_5$. In other embodiments, the receive mode may be defined by the time periods before $t_1$ and after $t_4$ and the transmit mode may be defined by the time period between $t_1$ and $t_4$. In some embodiments, $t_0$ may be equal to $t_1$. In some embodiments, $t_1$ may be equal to $t_2$. In some embodiments, $t_3$ may be equal to $t_4$. In some embodiments, $t_1$ may be equal to $t_5$.

The aspects of the present application may provide one or more benefits, some of which have been previously described. Now described are some non-limiting examples of such benefits. It should be appreciated that not all aspects and embodiments necessarily provide all of the benefits now described. Further, it should be appreciated that aspects of the present application may provide additional benefits to those now described.

Aspects of the present application provide pulsing circuits configured to generate bipolar pulses that may be received without resulting in the saturation of the receiving circuit. However receiving circuits may comprise components not designed to withstand the large positive and negative voltage spikes associated with the bipolar pulses.

Aspects of the present application provide symmetric switches configured to decouple the receiving circuit from the transmitting circuit, during a transmit mode, thus preventing damage to the receiving circuit caused by bipolar pulses.

The generation of time-domain and space-domain apodized pulses requires the ability to control multi-level pulses. Aspects of the present application provide feedback circuits configured to provide time-domain and space-domain apodization without resorting to additional supply voltages. Accordingly, incorporating additional supply voltages to the ultrasound devices may result in sizeable handheld ultrasound probes.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, and/or methods described herein, if such features, systems, articles, materials, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

The invention claimed is:

1. An ultrasound device comprising:
   at least one capacitive ultrasonic transducer;
   a pulser having an input terminal and an output terminal coupled to the capacitive ultrasonic transducer and configured to provide an input signal to the capacitive ultrasonic transducer having a value selected from among multiple selectable values;
   a feedback circuit coupled to the output terminal and the input terminal of the pulser and configured to provide a control signal to the input terminal of the pulser based on a comparison of a detection signal, representing or derived from the input signal, to a first threshold voltage of a plurality of comparison threshold voltages generated by the feedback circuit; and
   a dividing circuit configured to provide the detection signal to the feedback circuit, wherein a voltage of the detection signal is proportional to a voltage of the input signal.

2. The ultrasound device according to claim 1, wherein the pulser is configured to provide a bipolar input signal to the capacitive ultrasonic transducer.

3. The ultrasound device according to claim 1, wherein the pulser is configured to provide the input signal having a direct current (DC) component that is greater than zero.

4. The ultrasound device according to claim 1, wherein the feedback circuit comprises a resistive ladder configured to generate the plurality of comparison threshold voltages.

5. The ultrasound device according to claim 1, wherein the feedback circuit is configured to control the control signal to temporally apodize the input signal.

6. The ultrasound device according to claim 1, wherein the feedback circuit is digitally controlled.

7. The ultrasound device according to claim 1, wherein the feedback circuit is configured to provide the control signal to the pulser asynchronously.

8. The ultrasound device according to claim 1, where the capacitive ultrasonic transducer is a first capacitive ultrasonic transducer of a plurality of capacitive ultrasonic transducers, the pulser is a first pulser of a plurality of pulsers, the feedback circuit is a first feedback circuit of a plurality of feedback circuits, the control signal is a first control signal of a plurality of control signals and the input signal is a first input signal of a plurality of input signals;
   wherein the plurality of feedback circuits are configured to control the plurality of control signals to spatially apodize the plurality of input signals provided to the plurality of capacitive ultrasonic transducers.

9. The ultrasound device according to claim 1, wherein the capacitive ultrasonic transducer is coupled to bias circuitry and configured to receive a bias voltage having an absolute value that is greater than zero.

10. The ultrasound device according to claim 1, wherein the pulser comprises a first transistor exhibiting a first type of conductivity and a second transistor exhibiting a second type of conductivity different from the first type of conductivity.

11. A method of operating an ultrasound device having a capacitive ultrasonic transducer, a pulser coupled to the capacitive ultrasonic transducer, a dividing circuit, and a feedback circuit, the method comprising:
   with the pulser, providing an input signal to the capacitive ultrasonic transducer;
   with the dividing circuit, deriving a detection signal from the input signal, a voltage of the detection signal being proportional to a voltage of the input signal; and
   with the feedback circuit, generating a plurality of comparison threshold voltages and providing a control signal to the pulser to control the provision of the input signal based on a result obtained by comparing the detection signal to a first threshold voltage of the plurality of comparison threshold voltages.

12. The method of operating an ultrasound device according to claim 11, wherein the pulser is configured to provide a bipolar input signal to the capacitive ultrasonic transducer.

13. The method of operating an ultrasound device according to claim 11, wherein the pulser is configured to provide the input signal having a value selected from among multiple selectable values.

14. The method of operating an ultrasound device according to claim 11, wherein the pulser is configured to provide the input signal having a direct current (DC) component that is greater than zero.

15. The method of operating an ultrasound device according to claim 11, wherein the feedback circuit is configured to control the control signal to temporally apodize the input signal.

16. The method of operating an ultrasound device according to claim 11, wherein providing the control signal to the pulser to control the providing of the input signal is performed asynchronously.

17. The method of operating an ultrasound device according to claim 11, wherein the feedback circuit is digitally controlled.

18. The method of operating an ultrasound device according to claim 11, wherein the capacitive ultrasonic transducer is a first capacitive ultrasonic transducer of a plurality of capacitive ultrasonic transducers, the pulser is a first pulser of a plurality of pulsers, the feedback circuit is a first feedback circuit of a plurality of feedback circuits, the control signal is a first control signal of a plurality of control signals and the input signal is a first input signal of a plurality of input signals;
   wherein the plurality of feedback circuits are configured to control the plurality of control signals to spatially apodize the plurality of input signals provided to the plurality of capacitive ultrasonic transducers.

* * * * *